(12) United States Patent
Croft

(10) Patent No.: US 6,703,244 B2
(45) Date of Patent: Mar. 9, 2004

(54) METHOD FOR CONFIRMING PRESENCE OF MYCOTOXICOSIS

(76) Inventor: William A. Croft, N9178 County Rd. A, Crivitz, WI (US) 54935

( * ) Notice: Subject to any disclaimer, the term of this patent is extended or adjusted under 35 U.S.C. 154(b) by 391 days.

(21) Appl. No.: 09/908,873

(22) Filed: Jul. 20, 2001

(65) Prior Publication Data
US 2003/0017606 A1 Jan. 23, 2003

(51) Int. Cl.[7] .................. C12Q 1/04; G01N 33/569; G01N 30/90
(52) U.S. Cl. .................. 436/93; 436/161; 435/7.31; 435/34; 435/29
(58) Field of Search .............. 435/7.31, 35, 29; 436/93, 161

(56) References Cited

U.S. PATENT DOCUMENTS 4,772,551 A * 9/1988 Hart et al. ............... 435/7.31
5,118,612 A * 6/1992 Chu et al. ............... 435/7.93

* cited by examiner

*Primary Examiner*—Jill Warden
*Assistant Examiner*—Monique T. Cole
(74) *Attorney, Agent, or Firm*—Donald Cayen

(57) ABSTRACT

The present invention is a very significant way to determine exposure to toxic mold, or the disease called mycotoxicosis. Urine samples are extracted for trichothecene mycotoxins to confirm the disease of mycotoxicosis in humans. Diagnosis of mycotoxicosis is confirmable even when toxic mold exposure cannot be ascertained to a reasonable degree of certainty.

6 Claims, 1 Drawing Sheet

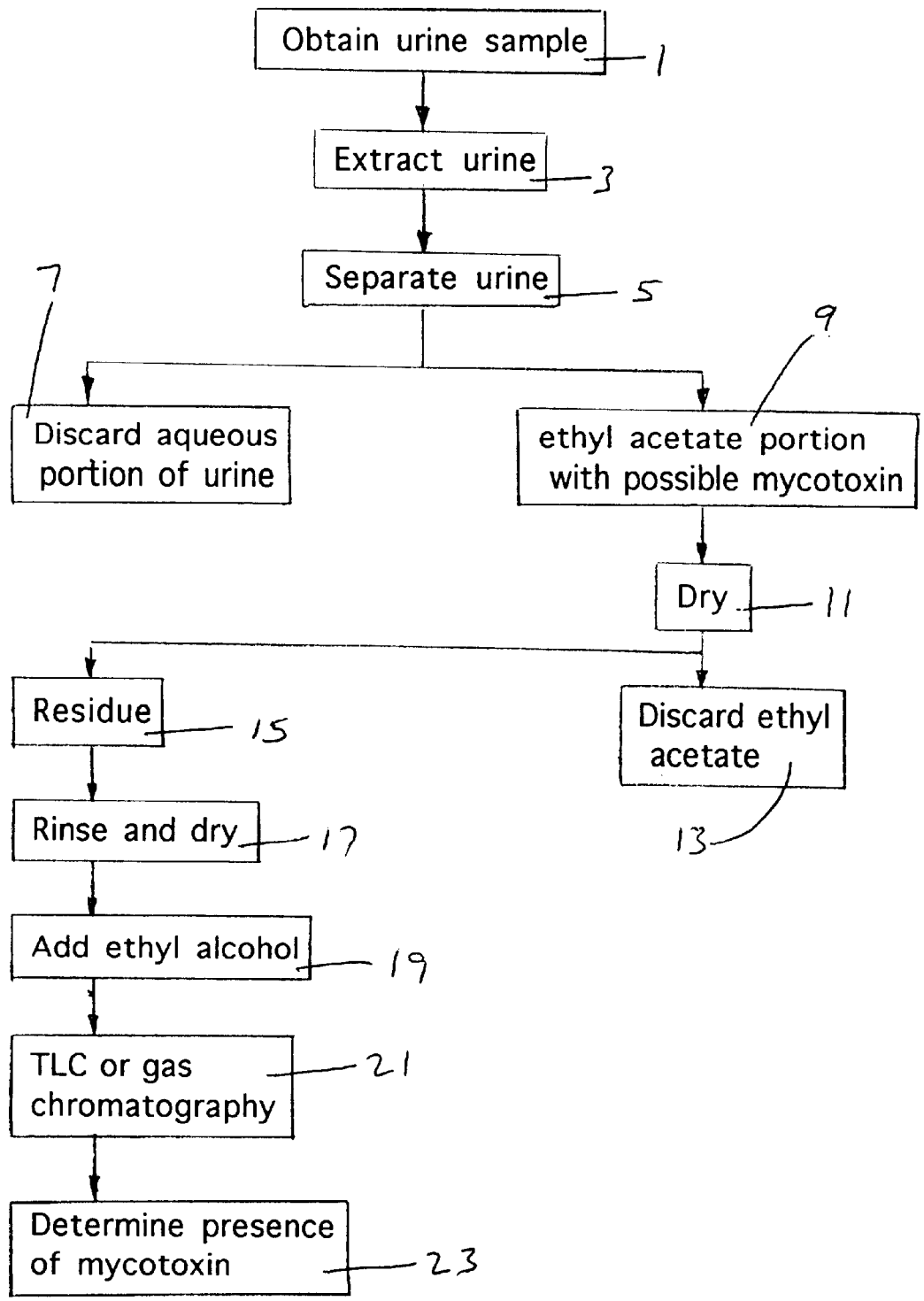

METHOD FOR CONFIRMING PRESENCE OF MYCOTOXICOSIS

BACKGROUND OF THE INVENTION

1. Field of the Invention

This invention pertains to human health care, and more particularly to a method for using a patient's urine to confirm the presence of mycotoxicosis in the person.

2. Description of the Prior Art

Trichothecene mycotoxins have been implicated in numerous cases concerning human health. Mycotoxins are found in the spores within the air, and they can be released as a vapor. The major case involving trichothecene mycotoxins occurred in an outbreak of Alimentary Toxin Aleukia near Orenburg, USSR, in the early 1940's. (Joffe 1971) (The cited references are fully described at the end of the detailed description of the invention. Other references of general but relevant interest are also fully cited.) The outbreak involved approximately ten percent of the population. Other cases have been reported that involved trichothecene mycotoxins in cereal grains that were contaminated by trichothecene producing fungi. (Ueno 1977, 1980, 1983) Trichothecene mycotoxins have also been identified in mold contaminated buildings that poisoned its inhabitants. A scientific paper entitled "Airborne Outbreak of Trichothecene Toxicosis" by William A. Croft, B. B. Jarvis, and C. S. Yatawara, Atmospheric Environment 20(3), 549–552 (1986) gives further background to the problems associated with mold contaminated buildings, and that paper is incorporated by reference herein. (Croft et al. 1986) In 1976, the scientific community acknowledged that poisoning by trichothecene mycotoxins is a commonly recognized disease.

Trichothecenes are cytotoxic to animals, humans, bacteria, and fungus, and they have a high affinity for eukaryotes cells. (Ueno 1977) They are known to inhibit protein synthesis at thirty parts per billion (PPB) and can affect every cell in the body. (Ueno 1977) Trichothecenes are used as biological warfare agents, because they can permanently disable people exposed to them. (Talmage 1983) In addition, trichothecenes are carcinogenic for man. (Costantini et al. 1998, 1999)

Trichothecenes mycotoxins have already been studied in animals. (Sato 1977, Ueno 1977) Prior data indicated that most of the mycotoxin administered in levels substantially less than the LD50 is eliminated relatively quickly through the feces and urine. (Talmage 1983) Higher levels of mycotoxin suggest interference with elimination via the gastrointestinal tract 0.8 percent and 17 percent in the urine. (Robison et al. 1979) The prior way to determine exposure of humans to toxic molds, or to the disease of mycotoxicosis, was based on the identification of mold within a building and then attempting to establish exposure. In the past, the medical community relied on mycologists to identify mold species growing in mold-contaminated buildings that caused human health maladies, and also to determine mold spore counts. (Johanning 1999) The prior methods led to confusion among health officials regarding diagnoses and safety issues.

Prior methods of testing for mold poisoning suffered the disadvantage of generating false positive or false negative test results based on mold antigen exposure. A false positive result can occur depending on the time of exposure. A brief mold exposure years earlier would generate antibodies that would still be present even though no mold exposure had occurred since.

A false negative result can exist if the blood is tested for the presence of mold antibodies. In order for the immune system to indicate the presence of mold exposure, it must generate antibodies against the exposed mold spores. The mycotoxin attacks the immune system, preventing the generation of antibodies. Therefore, testing for such a mold within the blood, and finding none, indicates no exposure to the mold. That result could well be a false negative.

Another possible cause of a false negative test result concerns the exposure to mycotoxins in the form of a vapor. When a person is exposed to mycotoxins as a vapor or gas, no antibodies are generated. Antibodies are made against spores or plant material, not against the mycotoxin. Accordingly, a test of the blood cannot detect any antibodies that would indicate exposure to molds. In fact, the person may have been exposed to molds, so the test result is a false negative.

Thus, a need exists for an improved method of determining human exposure to trichothecene mycotoxins and to mycotoxicosis.

References

Best, C. H., N. B. Taylor: The Physiological Basis of Medical Practice, A Text in Applied Physiology, $7^{th}$ Edition, The Williams & Wilkins Company, page 1286–1289 (1961).

Casarett and Doull's Toxicology, The Basic Science of Poisons, $5^{th}$ Edition, Curtis D. Klaassen, McGraw-Hill, Health Professions Division, page 122, 751 (1996).

Casarett and Doull's. Toxicology, The Basic Science of Poisons, McGraw-Hill, page 17–18 (1966)

Constantini A. V., Heinrick Weiland, and Lars I. Qvick: Fungalbionic Series, The Fungal/Mycotoxin Etiology of Human Disease, Etiology and Prevention of Prostate Cancer Hope at Last, Pub: Johan Friedrick Oberlin Verlag, Freiburg, Germany, (1998).

Costantini A. V., Heinrick Weiland, and Lars I. Qvick: Fungalbionic Series, The Fungal/Mycotoxin Etiology of Human Disease, Etiology and Prevention of Prostate Cancer Hope at Last, Pub: Johan Friedrick Oberlin Verlag, Freiburg, Germany, (1999)

Croft, W. A., B. B., Jarvis and C. S. Yatawara: Airborne Outbreak of Trichothecene Toxicosis, Atmospheric Environment 20(3), 549–552 (1986)

Cheville N. E.: Cell Pathology, The Iowa State University Press/Ames, page 3 (1976)

Edwards, W. C.: The diagnosis of petroleum hydrocarbon poisoning in cattle, Vet Med & Small Animal Clinician, 74 1516–1518 (1979).

Higuchi, S., T., Muramatsu, M., Satto, M., Sasao, K., Maruyama, and H., Kono: Ethanol Patch Test for Low Km Aldehyde Dehydrogenase Deficiency, The Lancet, March 14, 629 (1987).

Joffe A. Z.: Alimentary Toxic Aleukia. In Microbial Toxins, Vol. VII, edited by Kadis S., Ciegler A. and Ail S. J., page 139–189. Academic Press, Inc., New York (1971).

Johanning, E.: Bioaerosols, Fungi and Mycotoxins: Effects, Assessment, Prevention and Control, Eds. : Eastern New York Occupational and Environmental Health Center, Albany, New York (1999).

Pathre, S. V., and C. J. Mirocha: Assay methods for trichothecenes and review of their natural occurrence. In: Mycotoxins in Human and Animal Health. Eds.: Rodricks J. V., C. W. Hesseltine, and M. A. Mehlman, Pathotox Publishers, Park Forest South, Ill. Page 229–253 (1977).

Peters, Henry A., W. A. Croft, E. A. Woolson, B. A. Darcey, and M. A. Olson: Seasonal Arsenic Exposure From Burning Chrolnium-Copper-Arsonate-Treated Wood. JAMA 251 2393–2396 (1984)

Robison, T. S., C. J. Mirocha, H. J. Kurtz, J. C. Behrens, G. A. Weaver, and M. S. Chi: Distribution of tritium-labeled T-2 toxin into in swine. J. Agric. Food Chem. 27:1411–1413 (1979).

Sato, N., Y., Ueno: Comparative Toxicities of Trichothecenes, In: Mycotoxins in Human and Animal Health, Eds.: Rodricks J. V., C. W. Hesseltine, and M. A. Mehlman, Pathotox Publishers, Inc. page 295–397 (1977).

Talmage, D. W., Protection Against Trichothecene Mycotoxins, Committee on Protection Against Mycotoxins, Board on Toxicology and Environmental Health Hazards, Commission on Life Sciences, and National Research Council, National Academy Press, Washington, D.C. page, 128–129 (1983).

Ueno Y., Trichothecenes: overview address. In: Mycotoxins in Human and Animal Health, Eds.: Rodricks J., Hesseltine C. W. and Hehlman M. A., page 189–207. Pathotox, Inc., Park Forest South, Ill. (1977).

Ueno Y. : Trichothecene mycotoxins-mycology, chemistry, and toxicology. Adv. Nutr. Sci. 3, 301–353 (1980).

Ueno Y. : Trichothecenes-chemical, biological and Toxicological Aspects. Devel. Food Sci. 4, Elsevier, N.Y. (1983).

Umbreit, W. W., Modern Microbiology, The Basic Tools of Microbiology, page 30, 1962.

SUMMARY OF THE INVENTION

In accordance with the present invention, a method for confirming human and animal exposure to toxic molds, or to the disease of mycotoxicosis, is provided that is both reliable and simple. This is accomplished by analyzing the urine of persons and animals suspected of such exposure after they have spent some time in a contaminated environment.

Proof that mycotoxins are present is based on the following. Urine is extracted using ethyl acetate 60% V/40% V. If the person has indeed been exposed to trichothecene mycotoxins, the mycotoxin spots on thin layer chromatography (TLC) with displayed color and a relative frequency range (rf) of 0.2–0.6 using various solvents consistent with those reported in the scientific literature for trichothecene mycotoxins. The proof that this was the mycotoxin was to satisfy Koch's Postulates.

The method of the invention, using urine, is thus a very useful confirmatory test to identify mycotoxicosis in humans and animals. The probability of a false diagnosis is remote, even though the method is straight forward and easy to perform.

Other advantages, benefits, and features of the present invention will become apparent to those skilled in the art upon reading the detailed description of the invention.

BRIEF DESCRIPTION OF THE DRAWINGS

The drawing shows a flow chart of the extraction procedure according to the present invention.

DETAILED DESCRIPTION OF THE INVENTION

Although the disclosure hereof is detailed and exact to enable those skilled in the art to practice the invention, the physical embodiments herein disclosed merely exemplify the invention, which may be embodied in other specific methods. The scope of the invention is defined in the claims appended hereto.

The present invention is based on my discovery that mycotoxins can be extracted from human and animal urine. The present invention is a method that confirms the exposure to mycotoxins, and to the disease mycotoxicosis, by a person based on an analysis of his/her urine.

Mycotoxins are found in mold spores in the air, and they also can be released into the air as a vapor. I have discovered that exposure by a person to either form of the mycotoxins will show up in the person's urine. If the person is expressing signs and symptoms of mold exposure, definition of the mycotoxins in the urine confirms the presence of the disease mycotoxicosis. The urine test is sensitive enough to detect one PPB, confirming the disease.

The drawing shows in diagrammatic form the procedure used in carrying out the present invention. The first step, as shown in block 1, is to obtain a urine sample from the patient. For low level exposure to mycotoxins, at least 1,000 ml of urine is required. For high level exposure, at least 100 ml is required. The sample is taken after the maximum exposure of the person to a contaminated environment. For example, if the home is contaminated, the sample should be taken in the morning. If the workplace is contaminated, the sample should be taken at the end of the work period.

The urine sample is extracted, block 3, as by using ethyl acetate. The preferred extraction ratio is 60/40V/V. For example, if 1,000 ml of urine is used, the amount of ethyl acetate is 1,500 ml. The extracted urine is separated, block 5. For that purpose, I prefer to use a separator funnel. The resulting aqueous portion of the urine is discarded, block 7.

The remaining material from the extraction step of block 5 includes an ethyl acetate portion along with possible mycotoxins, block 9. That material is placed in a flask and taken to dryness, block 11. A rotovaporizer may be used.

The ethyl acetate is discarded, block 13. The remaining material, block 15, from the drying step, block 11, is rinsed from the flask, block 17, and placed in a vial, such as a 10 ml vial, and dried. For that drying step, a warming plate may be used. Five drops of 50–70% ethyl alcohol are added, block 19. The resulting material is placed on thin layer chromatograph or gas chromatograph, block 21. The procedure used for the TLC or gas chromatograph may be according to that described in the paper "Assay Methods For Trichothecenes and Review of Their Natural Occurrence" by S. V. Pathre and C. J. Mirocha as published in "Mycotoxins in Human and Animal Health," J. V. Rodricks, C. W. Hesseltine, and M. A. Mehlman, editors, Pathotox Publishers, Park Forest South, Ill., 229–253 (1997). Detection of any amount of trichothecene mycotoxins from 0.07 microgram or PPB will confirm the exposure and the disease of trichothecene mycotoxicosis, block 23.

For very high exposure to mycotoxins, direct application of several drops of a urine sample on thin layer plate can detect the mycotoxin.

Case 1

A family of four lived in an apartment in Nevada. An odor of mold or wet wood was present. The family members suffered chronic malaise and fatigue, among other health problems including severe headaches, asthma, diarrhea, respiratory distress, and skin rashes. A Hepa air filtering unit was used to clean the air in the apartment.

Based on the signs and symptoms expressed by the family, it was thought that the family had been exposed to mycotoxins. Urine samples were collected from the family members. The urine samples exhibited no bacterial growth or putrification at room temperature for five months, antibiotic activity. The color of the urine did not change. Large amounts of protein were observed in the bottom of the urine container. Dark brown, black coloring (scale of 2–3) on the sulfuric acid test indicated mycotoxin was present. Urine collected and extracted for mycotoxin revealed substantial levels of mycotoxin, which was injected into weanling rats. 10.2 grams of black, syrupy material were submitted to independent researchers, who confirmed, with the use of animals, that the material contained high levels of trichothecene mycotoxins. The Hepa filter was removed from the apartment and a chemical extraction on the filter was performed. Using thin layer chromatography, the extract color and relative frequency (rf) (0.2–0.6 various solvents) were consistent with those reported in the literature for trichothecene mycotoxins. Mycotoxin extracted from the Hepa filter was spotted on thin layer chromatography and treated with six percent sodium hypochlorite solution. The solution had no effect on the spotted mycotoxin (0.5–1.5 ug/spot) compared to untreated mycotoxin; the relative frequency (rf, 0.43) did not change. (Higuchi et al. 1987, Best et al. 1961, Pathre et al. 1977)

Case 2

The home of a family of four in Kentucky caught fire, resulting in substantial water and fire damage. After repairs, including repairs to sub-floor venting ducts, the family moved back into their home. Over the next six years, the family's health deteriorated. The mother was diagnosed with rapid heartbeat and severe asthma. She was given a few months to live. The father suffered numerous psychological manifestations and agoraphobia. The children could not tie their shoes or ride their bicycles very well, and they appeared stunted in their development. All the family members suffered the signs and symptoms typical of mold exposure that involved the respiratory system with severe congestion of lungs and sinuses including cerebellar disease. All the members expressed flu-like symptoms, nausea, vomiting, bloating, abdominal distention and pain, excessive flatus, and moderate diarrhea. All reported skin rashes, infection, and skin growth. They also suffered from moderate to severe malaise and fatigue, wanting to sleep 16–18 hours per day with an inability to control body temperature. They all reported easy bruising and extended bleeding of skin cuts, allergies to molds. They did not have skin edema or hemorrhaging within the skin. They also expressed skin growths 0.3–0.6 centimeters in diameter that were epithelial in origin.

Urine samples were taken from the family members. The urine collected from each member was observed as no growth, antibiotic, sulfuric acid color was dark brown, black, scale 2–3, contained trichothecene mycotoxin. Extracted mycotoxin spotted on TLC displayed color and a range (rf) of 0.2–0.6 using various solvents, was consistent with those reported in the literature for trichothecene mycotoxins. The mycotoxins extracted from each urine specimen was injected into weanling rats and the observed pathology matched the signs and symptoms reported.

Mold bulk samples were taken from ceiling fan blades loaded with sticky dust build up. The dust samples were submitted for mold spore identification. The family members were exposed to Penicillium sp. and Cladosporium sp. that were detected in the cold air return ducts within their home. (Best et al. 1961)

Case 3

A 55 year old lady was disease free with no allergies when she moved into a new apartment in Wisconsin. Months later she developed severe immune depression. Her health gradually declined over approximately 13 years. Her mental processes also deteriorated. Despite the fact that the apartment was very clean, she expressed signs and symptoms of trichothecene mycotoxins exposure.

Urine was collected from the patient. The urine demonstrated no growth, antibiotic activity, dark brown, black, scale of 2–3, on the sulfuric acid test. Extracted mycotoxin spotted on TLC displayed color and a range of (rf) 0.2–0.6 using various solvents, was consistent with those reported in the literature for trichothecene mycotoxins. Severe amounts of protein were observed in the urine sample. Extracted mycotoxin from the urine and injected into rats clearly demonstrated degeneration and necrosis of the rats' organs that matched the patient's signs and symptoms. (Croft et al. 1986)

Case 4

496 tenant families lived in an apartment located in New York. The tenants reported many degenerative diseases, various cancers, unexpected deaths, and signs and symptoms typical of mold exposure as reported in my previously mentioned paper "Airborne Outbreak Of Trichothecene Toxicosis."

Examination of the apartments revealed severe mold growth in more than 73 apartments. It was so substantial that bulk mold samples were taken for identification with ease, using forceps. Mold growth was observed in most rooms of each apartment, the heaviest growth being in bathrooms and kitchens. Door sills, hallways, elevator shafts, and ventilating ducts were heavily contaminated with mold spores. There was a very strong odor of mold vapors detected within the building, including most apartments. Black mold spores were detected flowing across the floor by elevator doors when the elevator was in use. Outside walls were open to water damage and mold growth, and wind and rain penetrated the walls. Water was reported running onto apartment floors during rain storms.

Urine samples were collected from 21 tenants and extracted for mycotoxins. The urine samples exhibited no growth, antibiotic activity, or marked amount of protein. The sulfuric acid tests were ranged from gray to black, scale of 1–3 reflective of urine volume and concentration. Extracted mycotoxin spotted on TLC displayed color and a range of (rf) of 0.2–0.6 using various solvents, was consistent with those reported in the literature for trichothecene mycotoxins. The urine was extracted for mycotoxin, prepared for injection into test animals, and a ratio of 1 ml of 50 percent ethanol to 100 ml of urine extracted based on acute toxicity in several animals was determined and compared to the three cases described above. The level of mycotoxin activity excreted in the patients in Case 4 was three times higher than for the other three case study groups examined.

The mycotoxin was injected into weanling female rats. The rats displayed depression, lack of eating, diarrhea and decreases in spontaneous movement and body temperature cold to the touch. Examination of the tissues revealed degeneration and necrosis in all the organs examined: brain, thymus, eye, eye glands, lungs (hemorrhage), heart, intestines, lymph nodes, arteries, liver, pancreas, spleen, kidneys, adrenal, ganglion, bone marrow, and spinal cord, all correlating with the signs and symptoms expressed by the patients and thereby reproducing the disease in the animals. Negative control rats did not display any ill health. (Croft et al. 1986, Pathre et al. 1977, Ueno 1977, Joffe 1971, Best et al. 1961, Sato 1977)

Discussion

In view of the four cases studied, when urine was collected and extracted for trichothecene mycotoxins, the urinary tests confirmed the observed signs and symptoms and the diagnosis of mycotoxicosis even when the mold exposure could not be established to a reasonable degree of scientific certainty. In Case 1, the Nevada family had extensive signs and symptoms and their clothing was even treated with six percent sodium hypochlorite to neutralize the mycotoxin. The urine test clearly revealed that the mycotoxin was not altered and the people still remained exposed to high levels of mycotoxins, which are known to be cumulative in their poisoning effects. (Joffe 1971)

The second case, involving the Kentucky family, clearly showed exposure to trichothecenes, which was detected in high levels in each family member even though an obvious mold site was not found. It had to be that of the floor vents, which contributed to the high release of spores when the venting fans were turned on that had Penicillium sp. and Cladosporium sp. growing for months in high moisture organic matter. In sub-lethal doses administered to animals the involuntary movement and body temperature is lost, and those conditions were very obvious in the Kentucky family. (Sato et al. 1977)

The third case of the lady in Wisconsin, in which the apartment was well kept and no obvious mold growth could be detected until the cold air return duct and associated wall revealed faulty construction, no moisture barrier, allowing moisture to accumulate. The detection of the mycotoxin within the lady's urine and reproducing the disease in animals confirmed the diagnosis that this lady had been suffering with this mystery health malady for 13 years. (Joffe 1971)

The fourth case, involving the large apartment complex in New York, and the extraction of urine from 21 different families, established that trichothecenes caused severe health problems that matched the signs and symptoms expressed by the residents. The residents excreted approximately three times higher mycotoxin activity levels than in the other three cases. (Joffe 1971)

In all four cases the signs and symptoms expressed by the patients established a commonly recognized disease. (Ueno 1977) Identification of the type of mold growing or spore counts could not establish the level of exposure. The collection of urine from the patients and the extraction of mycotoxin clearly revealed the exposure to the mycotoxins in each case. The reproduction of the disease or poisoning with the animals fulfilled Koch's Postulants conditions and established the cause of the disease. (Croft et al. 1986, Ueno 1983, Joffe 1971, Umbreit 1962) Each poison expresses a fingerprint as signs and symptoms or pathology to confirm the causative agent. (Cheville 1976)

The mycotoxin can be released as a gas or vapor in which spore identification or spore counts are not able to establish exposure, but a urine sample will express exposure to vapors of the mycotoxin detected within the urine. The excretion of trichothecene has been examined in several species of animals. These data indicate that most of the mycotoxin administered in levels substantially less than the LD50 is eliminated relative quickly through the feces and urine. (Talmage 1983) In this study, urine levels of mycotoxin excreted reflect exposure levels and based on the rat toxicity the New York tenants exposed to severe mold conditions excreted three times the mycotoxin levels of the other three cases. The test for mycotoxins in the urine thus becomes a useful tool to confirm exposure to trichothecenes at low levels over a chronic period in patients.

In summary, the results and advantages of urine testing can now be more fully realized. The method of the invention confirms or denies the diagnosis of mycotoxicosis caused by trichothecene mycotoxins in man, especially in cases where exposure or source are at question. This desirable result comes from recognizing the possibility that urine testing of animals exposed to mycotoxins might be applicable to humans. The method of the invention establishes that human urine can indeed reveal exposure to mycotoxins.

It will also be recognized that in addition to the superior performance of the present invention, its method is such as to have widespread application throughout the world. Analysis of urine samples at a reasonable cost is well within the capability of central laboratories and hospitals.

Thus, it is apparent that there has been provided, in accordance with the invention, a method for confirming presence of mycotoxicosis that fully satisfies the aims and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A method for confirming the presence of trichothecene mycotoxins in a person comprising the steps of:
   a. collecting a sample of urine from a person;
   b. extracting the urine using a predetermined ratio by volume of urine and ethyl acetate;
   c. separating the extracted urine into an aqueous portion of the urine and an ethyl acetate portion, and discarding the aqueous portion of the urine;
   d. drying the ethyl acetate portion to produce a residue;
   e. rinsing and drying the residue;
   f. adding ethyl alcohol to the residue;
   g. subjecting the ethyl alcohol and the residue to thin layer chromatography or gas chromatography; and
   h. observing the ethyl alcohol and the residue subjected to the thin layer chromatography or gas chromatography for the presence of mycotoxins and thereby confirming or denying exposure of the person to mycotoxins.

2. The method of claim 1 wherein the predetermined ratio by volume of urine and ethyl acetate is approximately 60/40V/V.

3. The method of claim 1 wherein the step of collecting a sample of urine comprises the step of collecting a sample of between approximately 100 milliliters and 1,000 milliliters of the urine.

4. The method of claim 1 wherein the step of separating the extracted urine comprises the steps of depositing the extracted urine in a separator funnel, and operating the separator funnel to separate the extracted urine into the aqueous portion of the urine and the ethyl acetate portion.

5. The method of claim 1 wherein the step of drying the ethyl acetate portion comprises the steps of depositing the ethyl acetate portion in a rotovaporizer, and operating the rotovaporizer to dry the ethyl acetate portion.

6. The method of claim 1 wherein the step of adding ethyl alcohol to the residue comprises the step of adding approximately five drops of 50–70 percent ethyl alcohol to the residue.

* * * * *